United States Patent [19]

Goldstein

[11] 4,002,602

[45] Jan. 11, 1977

[54] UBIQUITOUS IMMUNOPOIETIC POLYPEPTIDE (UBIP) AND METHODS

[76] Inventor: Gideon Goldstein, 4455 Douglas Ave., Riverdale, N.Y. 10471

[22] Filed: Aug. 22, 1975

[21] Appl. No.: 606,844

Related U.S. Application Data

[63] Continuation-in-part of Ser. No. 449,686, March 11, 1974, abandoned.

[52] U.S. Cl. .......................... 260/112.5 R; 424/177
[51] Int. Cl.$^2$ ................. C07C 103/52; C07G 7/00; A61K 37/00
[58] Field of Search ............................ 260/112.5 R

[56] References Cited

UNITED STATES PATENTS 3,951,939  4/1976  Fritz et al. ..................... 260/112

Primary Examiner—Lewis Gotts
Assistant Examiner—Reginald J. Suyat
Attorney, Agent, or Firm—Lowe, King, Price & Markva

[57] ABSTRACT

There is disclosed a new Ubiquitous Immunopoietic Polypeptide (UBIP) which has been isolated in fluffy white powder form from bovine thymus but which has been found to be present in living cellular tissue of all animals and plants tested including various guinea pig tissues, cells in tissue cultures and tissues from birds, fish, squid, plants, fungi and bacteria, the polypeptide being characterized by its ability to induce in vitro, in nanogram concentrations, the differentiation of both T cell and B cell immunocytes from precursors present in bone marrow or spleen and thus the polypeptide is useful in therapeutic areas involving thymic or immunity deficiencies and the like. The polypeptide also exhibits hypotensive properties. The polypeptide is isolated from living source materials by a combination of sizing techniques and ion-exchange chromatography and may be described by the following amino acid structural sequence:

$H_2N$-MET-GLN-ILE-PHE-VAL-LYS-THR-LEU-THR-GLY-LYS-THR-ILE-THR-LEU-GLU-VAL-GLU-PRO-SER-ASP-THR-ILE-GLU-ASN-VAL-LYS-ALA-LYS-ILE-GLN-ASP-LYS-GLU-GLY-ILE-PRO-PRO-ASP-GLN-GLN-ARG-LEU-ILE-PHE-ALA-GLY-LYS-GLN-LEU-GLU-ASP-GLY-ARG-THR-LEU-SER-ASP-TYR-ASN–ILE-GLN-LYS-GLU-SER-THR-LEU-HIS-LEU-VAL-LEU-ARG-LEU-ARG-COOH

12 Claims, 4 Drawing Figures

UBIQUITOUS IMMUNOPOIETIC POLYPEPTIDE (UBIP) AND METHODS

CROSS-REFERENCE TO RELATED APPLICATIONS

This is a continuation-in-part of copending Application Ser. No. 449,686, filed Mar. 11, 1974 now abandoned.

The invention described herein was made in the course of work under a grant or award from the Department of Health, Education and Welfare.

BACKGROUND OF THE INVENTION

FIELD OF THE INVENTION

This invention relates generally to a new polypeptide and more particularly to a new polypeptide isolated in purified form from the bovine thymus but present in cells of all species tested, to methods for isolation of the new polypeptide, and therapeutic methods and fields of use for the polypeptide.

DESCRIPTION OF THE PRIOR ART

It is known that various polypeptides have been isolated from the organs of animals. Until about the past decade, however, very little was known about the thymus, an organ which in man comprises about 0.8% of his body weight at birth, although it has been previously hypothesized that a neuromuscular blocking substance existed in the thymus. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus is known to be a compound organ consisting of an epithelial stroma derived from the third bronchial arch and lymphocytes are derived from stem cells originating in haemopoietic tissues, Goldstein et al, *The Human Thymus*, Heinemann, London, 1969. Lymphocytes are differentiated within the thymus and leave as mature thymus-derived cells, called T cells, which circulate to the blood, lymph, spleen and lymph nodes. The induction of stem cell differentiation within the thymus appears to be mediated by secretions of the epithelial cells of the thymus but difficulties with bioassays had hindered the complete isolation and structural characterization of any hormones which may be present.

It has been known for some time that the thymus is connected with the immunity characteristics of the body and therefore great interest has been indicated in substances which have been isolated from the thymus. In this regard, there have been published in recent years a relatively large body of articles based on scientific work relating to materials which are present in bovine thymus. In fact, the Applicant has published a number of articles which relate to his research in this area. Pertinent publications may be found for example in *The Lancet*, July 20, 1968, pps. 119–122; *Triangle*, Vol. 11, No. 1, pps. 7–14, 1972; *Annals of The New York Academy of Sciences*, Vol. 183, pps. 230–240, 1971; and *Clinical and Experimental Immunology*, Vol. 4, No. 2, pps. 181–189, 1969, and *Nature*, Vol. 247, pps. 11–14, (1974).

In the article by Goldstein and Manganaro in *Annals of the New York Academy of Sciences*, Vol. 183, pps. 230–240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin", was believed to cause myositis but it was further indicated that this polypeptide had not been isolated although it appeared to be a polypeptide of approximately 7,000 molecular weight, had a strong net positive charge and was retained on CM-Sephadex at pH of 8.0.

It was further disclosed that small amounts of a material named "thymin" had been detected in bovine thymus using saline extraction, heat treatments, centrifugation, ion exchange chromatography, molecular sieving on Sephadex, hydroxyl apatite chromatography and preparative polyacrylamide electrophoresis. At page 235, it was indicated that neuromuscular blocking activity had been detected in a polypeptide fraction of approximately 7,000 molecular weight and that doses of 0.2 milligram of this material injected subcutaneously in 200 gram rats caused myasthenic neuromuscular block at 5 days as demonstrated by electromyography. The polypeptide of the present invention is not disclosed by these prior art disclosures.

In Applicant's Application, Ser. No. 429,202, filed Dec. 28, 1973, there is disclosed the isolation of highly pure polypeptides which are different from substances disclosed in the prior articles and which have been isolated in a form which did not exist in the bovine thymus from where they were obtained. Further, the polypeptides isolated from bovine thymus in accordance with that invention exhibit physiological characteristics which suggest their importance to medical science in the study of the immunity system of the human body and they have many therapeutic applications. These findings were subsequently published in *Nature*, Vol. 247, pps. 11–14 (1974).

The present invention relates to a new polypeptide, termed "Ubiquitous Immunopoietic Polypeptide", (UBIP), which was discovered during Applicant's investigation of substances contained in bovine thymus. This new polypeptide has been found to be a different material from all polypeptides known previously and to exhibit distinctive important physiological characteristics and advantages.

SUMMARY OF THE INVENTION

It is accordingly one object of this invention to provide a new polypeptide which is important biologically.

A further object of the invention is to provide a new polypeptide identified as Ubiquitous Immunopoietic Polypeptide (UBIP) which has the characteristics of stimulating the differentiation of T cell and B cell immunocytes, and is thus highly useful in the immunity system of humans and animals and in other areas.

.. A further object of the invention is to provide methods for isolating, separating and characterizing the novel polypeptide of this invention, as well as compositions and methods for its use in biological activities.

Other objects and advantages of the invention will become apparent as the description thereof proceeds.

In satisfaction of the foregoing objects and advantages there is provided by this invention a highly pure polypeptide in the physical form of a white or light-colored fluffy powder which may be characterized as having a molecular weight of about 9,000 dalton, a major L-amino acid sequence in which there may be minor variations or substitutions depending on the source materials, said polypeptide being present in and isolatable from living cellular materials of animals, plants, fungi and bacteria, the polypeptide being characterized by a relative mobility on disc electrophoresis on 7% polyacrylamide gel of about 0.76 with respect to methyl green at a pH of 4.3, and a relative mobility on disc electrophoresis on 7% polyacrylamide gel of about 0.26 with respect to bromphenol blue at a pH of 8.9, said polypeptide being characterized by its ability to stimulate the differentiation of both T cells and B cells in subnanogram concentrations, the polypeptide being isolated from cellular materials by procedures involving molecular sizing techniques and ion-exchange chromatography.

BRIEF DESCRIPTION OF THE DRAWING

Reference is now made to the drawings accompanying this application wherein.

DESCRIPTION OF PREFERRED EMBODIMENTS

Figure 1:
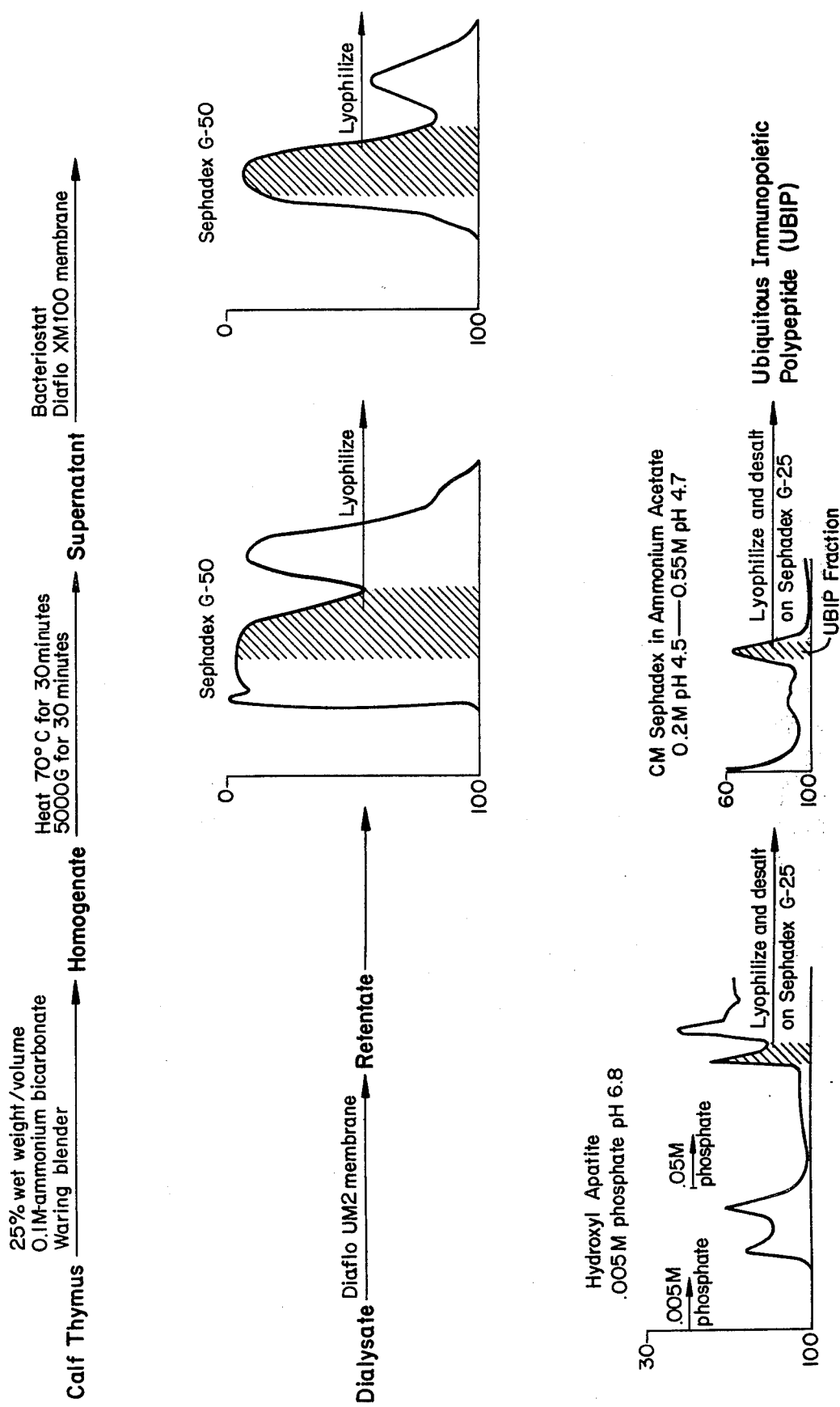
FIG. 1 is a graph which shows the isolation of the polypeptide from bovine thymus by a specific procedure and the peak of the polypeptide as measured by ultraviolet absorbence.

As indicated above, this invention is concerned with a new polypeptide, its method of isolation and areas of use. This new polypeptide has been obtained in the physical form of a white or light-colored fluffy powder and has been determined to have a number of unique characteristics and physiological actions. For these reasons, the polypeptide has been termed a Ubiquitous Immunopoietic Polypeptide or the acronym UBIP. It's purity has been characterized by its relative mobility on disc electrophoresis. Many of its physiological and biological actions have also been assessed.

The polypeptide was originally isolated from bovine thymus as a fluffy white powder. It has subsequently been found that the polypeptide is present in all living cells tested including various tissues of guinea pig, various cells in tissue culture and tissues obtained from birds, fish, squid, plants, fungi and bacteria. Thus, it appears to be present in all living cells and that all living cells, both plants, animals, fungi and bacteria, can serve as a source of the Ubiquitous Immunopoietic Polypeptide (UBIP) of this invention. The polypeptide isolated from human thymus has been found to have the same amino acid sequence as that isolated from bovine thymus.

The polypeptide isolated from bovine thymus has also been characterized by its L-amino acid sequence. However, as there may be minor variations in the amino acid sequence depending on the cellular source, the present invention is deemed to cover any such sequence variations and therefore the invention is not to be considered as limited to this precise sequence.

The polypeptide isolated from bovine thymus has been determined to have the following L-amino acid sequence:

$H_2N$-MET-GLN-ILE-PHE-VAL-LYS-THR-LEU-THR-GLY-LYS-THR-ILE-THR-LEU-GLU-VAL-GLU-PRO-SER-ASP-THR-ILE-GLU-ASN-VAL-LYS-ALA-LYS-ILE-GLN-ASP-LYS-GLU-GLY-ILE-PRO-PRO-ASP-GLN-GLN-ARG-LEU-ILE-PHE-ALA-GLY-LYS-GLN-LEU-GLU-ASP-GLY-ARG-THR-LEU-SER-ASP-TYR-ASN-ILE-GLY-LYS-GLU-SER-THR-LEU-HIS-LEU-VAL-LEU-ARG-LEU-ARG-COOH

In the above structures, the amino acid components of the peptides are identified by abbreviations for convenience. These abbreviations are as follows:

| Amino Acid | Abbreviated Designation |
|---|---|
| L-methionine | MET |
| L-arginine | ARG |
| L-alanine | ALA |
| L-glutamine | GLN |
| L-aspartic acid | ASP |
| L-glutamic acid | GLU |
| L-histidine | HIS |
| L-proline | PRO |
| L-lysine | LYS |
| Glycine | GLY |
| L-leucine | LEU |
| L-phenylalanine | PHE |
| L-isoleucine | ILE |
| L-asparagine | ASN |
| L-serine | SER |
| L-tyrosine | TYR |
| L-threonine | THR |
| L-valine | VAL |

In general, the polypeptide of this invention can be obtained or isolated by a combination of molecular sizing techniques, that is, by membrane and/or molecular sieve chromatography followed by ion exchange chromatography to obtain further separation by charge. The sizing techniques are used to separate materials based on the molecular weight size so as to ultimately obtain materials having molecular weights within a definite range, in this instance, within a range of about 4,000 to 12,000 dalton. The sizing techniques are carried out by contact with or passage of the source materials, usually in homogenized form, through a membrane or in contact with a molecular sieve in which the openings in the membrane or pores within the molecular sieve will retain substances within a particular molecular weight or will repel substances having a particular molecular weight. Thereafter, in the present instance, after a substance is obtained which has a molecular weight in the range of 4,000–12,000 dalton, it is treated one or more times using ion exchange chromatographic procedures. The ion exchange chromatography can be carried out with cation exchangers, such as those based on cross-linked dextrans, (e.g. CM-Sephadex or SP-Sephadex), over a wide range of pH (4.0–6.0) and concentrations (0.01–1.0M). Also anion-exchangers such as DEAE-Sephadex or QAE-Sephadex may be used over a range of pH (7.5–11.0) 0 and concentrations (0.01–1.0M). Ion exchange chromatography is carried out to the extent required to obtain a product having a molecular weight in the range of about 9,000 dalton and result in isolation of the polypeptide product of this invention. It should be understood, of course, that the sizing techniques and ion exchange chromatography steps can be carried out as many times as desired in order to obtain a highly purified product. The separations mentioned can be used alternatively or sequentially in order to achieve a product of greater purity.

Unlike the products disclosed in the above-identified copending application, the polypeptide of this invention does not cause any detectable neuromuscular lesions in the electromyographic assay used to monitor the isolated products obtained in these previous procedures. It was found, however, that the polypeptide of this invention induces the differentiation of immunocyte-precursor cells in vitro although its effect is clearly distinguishable from that of the products described in my copending patent application or of other substances disclosed in the prior art. Thus, the polypeptide of this invention, even in nanogram concentrations, has been found to induce the differentiation of both T-precursor cells as measured by the acquisition of the thymic differentiation antigens TL and THY-I ($\theta$), as well as B-precursor cells as measured by the acquisition of receptors for complement, a distinctive marker of B cells. By contrast the Thymin products of my copending application were found to induce the differentiation of T-precursor cells but not of B-precursor cells. The polypeptide of this invention also exhibits hypotensive activity, a further distinction from the products disclosed and claimed in the copending application.

The induction of T cell differentiation by extracts of tissues other than thymus has been reported previously in *Journal of Experimental Medicine*, 138, pps. 1027–1032, 1973. The present finding that the polypeptide of this invention is a potent inducer of immunocyte differentiation, and is ubiquitous in body tissues, emphasizes the problem of specificity if such immunological differentiation assays are used to monitor the fractionation of thymus extracts for the isolation of thymic hormones. The finding that the polypeptide of this invention can induce the differentiation of immunocytes at such low concentrations suggests that receptors for this polypeptide are present on immunocyte precursor cells. However, in view of the apparent wide-spread distribution of the polypeptide in the body it is uncertain whether this polypeptide acts physiologically as an immunopoietic hormone or whether it has an entirely different primary function.

To provide an understanding of the importance of the differentiating biological characteristics of the polypeptide of this invention, it should be noted that the function of the thymus in relation to immunity may be broadly stated as the production of thymus-derived cells, or lymphocytes, which are called T cells. T cells form a large proportion of the pool of recirculating small lymphocytes. T cells have immunological specificity and are directly involved in cell-mediated immune responses (such as homograft responses), as effector cells. T cells, however, do not secrete humoral antibodies as these antibodies are secreted by cells derived directly from the bone marrow independently of the thymic influence and these latter cells are termed B cells. However, for many antigens, B cells require the presence of appropriately reactive T cells before they can produce antibodies. The mechanism of this process of cell cooperation is not yet completely understood.

From this explanation, it may be said that in operational terms, the thymus is necessary for the development of cellular immunity and many humoral antibody responses and it affects these systems by inducing, within the thymus, the differentiation of naemopoietic stem cells to T cells. This inductive influence is mediated by secretions of the epithelial cells of the thymus, that is, the thymic hormones, including Thymin I and Thymin II, (claimed in my copending U.S. Application, Ser. No. 429,202, filed Dec. 28, 1973).

Further, to understand the operation of the thymus and the cell system of lymphocytes, and the circulation of lymphocytes in the body, it should be pointed out that stem cells arise in the bone marrow and reach the thymus by the blood stream. Within the thymus, stem cells become differentiated to immunologically competent T cells, which immigrate to the blood stream and together with B cells, circulate between the tissues, lymphatics and the blood stream.

The cells of the body which secrete antibody also develop from hemopoietic stem cells but their differentiation is not determined by the thymus. Hence, they are termed bone marrow-derived cells or B cells. In birds they are differentiated in an organ analogous to the thymus, which is called the Bursa of Fabricius. In mammals no equivalent organ has been discovered and it is thought that B cells differentiate within the bone marrow. The physiological substances dictating this differentiation remain completely unknown.

As indicated above, the polypeptide of this invention has been identified as being present in all living cellular materials tested and a general procedure for isolating the polypeptide has been set forth. The product has been obtained in highly purified form from bovine thymus utilizing a more specific series of steps, the specific steps involving purification and separation within the broad process indicated. Generally, this more specific process involves obtaining fresh clean disected bovine thymus which has been stored at temperatures of less than 0° C., i.e., about −30° to −10° C. In conducting the process, a batch of the thymus is initially homogenized at about 20–30% wet weight per volume of a buffered saline solution and good mixture obtained to the point of homogenization by the presence of agitation. The buffered saline can include any of the well known solutions which are used for this purpose including sodium and potassium phosphate buffered salt solutions and in general, any of the alkali metal or ammonium salt solutions. The solution should have a concentration of about 0.05M to 0.2M. A particularly preferred solution is an ammonium bicarbonate aqueous solution of about 0.1M. The resulting homogenized extract is then heated at a temperature of about 60–90° C. for about 15 minutes up to about 1 hour depending on the temperature used in order to homogenize the mixture as much as possible. Thereafter, any nonhomogenized material is removed by any suitable method, e.g. high speed centrifugation, for ¼ hour to about 1 hour. The resulting supernatant is then filtered or centrifuged in order to remove any insoluble materials and since the remaining steps are usually carried out at room temperature, it may be necessary to add a commercial bacteriostat to the mixture at this point in order to prevent contamination. If the process is carried out in a cold room or at low temperatures, for example around 4° C., the bacteriostatic agent can be omitted.

The resulting mixture is then separated according to molecular size, preferably with the use of membranes in order to separate materials present in the mixture on the basis of size. The purpose of this separation is to use a membrane which will permit the polypeptide compounds to pass through the membrane while holding up larger molecular weight materials. As indicated, since the desired polypeptide has a molecular weight within the range of about 4,000 to 12,000 dalton it is sufficient for purposes of this step to prevent passage through the membrane of materials which have molecular weights of, for example, above about 100,000 dalton. Membranes such as Diaflo XM100 membrane, and methods for the use of such membranes to effect the separation, are known in the art.

After this step, the solution which passed through the membrane, the dialysate, which contains the desired products, is then subjected to further enrichment on the basis of molecular size by passing the extract through a membrane under dialysis conditions which will prevent the higher molecular weight materials from passing through but permits the smaller molecular weight materials present in the extract to pass through the membrane. Thus, in this step, materials having molecular weights in the range of about 2,000 to 100,000 dalton are prevented from passing through the membrane by selection of a membrane for this purpose (such as Diaflo XM100) in accordance with known procedures while permitting materials of smaller molecular weight to pass through.

In this step of the procedure a major reduction in volume is obtained in that after completion of this dialysis the volume of the extract is reduced so that less than 1% by volume of the extract is retained for the next step.

The resulting retentate is then fractionated by molecular exclusion chromatography using molecular sieves to effect the fractionation. In this step, a molecular sieve is used for the chromatographic operation which has a pore size such that materials having molecular weights above about 30,000 are totally excluded from the pores and pass through the chromatographic column rapidly. The pore size is selected so that materials having a molecular weight of less than about 1,500 will be totally permeable within the pores and fully retarded on the column. A molecular sieve which is very suitable for this purpose is a commercial product G50-medium Sephadex, a molecular sieve based on cross-linked dextran and which is very effective on a column of about 2.5 by 100 centimeters in size. The number "G-50" indicates pore size. From this fractionation step there is collected an extract which has a molecular weight in the range of about 4,000 to about 12,000.

The extract is collected since it is partially excluded from the sieve pores and the separation is made by usual chromatographic techniques. The resulting fractions are lyophilized and rerun through the same system, that is, again through the molecular sieves in order to effect as good a separation as possible and obtain only materials having molecular weights in the range of 4,000–12,000. It should be understood of course, that the steps involving the molecular sieving may be repeated as many times as necessary or desirable and in fact any of these steps may be repeated in order to enhance purification. According to this invention, it has been found that two passages by molecular sieve chromatograhy are usually sufficient.

After the fractions are removed from the molecular sieve column and lyophilized they are preferably then fractionated by adsorption chromatography in order to increase purification. The adsorption chromatography step is preferably carried out by dissolving the extract in a 0.001M to 0.008M, preferably 0.005M, phosphate buffer solution at a pH of approximately 6.8 and passing through a column containing hydroxyl apatite. In conducting this step, Thymin I and Thymin II, the active fractions disclosed in my copending U.S. Application, Ser. No. 429,202, will be eluted behind the void volume with 0.005M phosphate buffer. To obtain the product of this invention, the concentration of the eluting buffer is then raised to 0.05M, the resulting fraction is lyophilized and desalted on a molecular sieve column in which the salts are retained in the pores and the active material (UBIP) is excluded in the void volume. The principle of this separation by adsorption chromatography is that differential sticking on the hydroxyl apatite is obtained. Thus, in this step the hydroxyl apatite retards the fraction of interest which is then removed, lyophilized and desalted as indicated. This step may alternatively be omitted from the procedure although it does provide a product of higher purity.

The resulting material is then fractionated further by ion exchange chromatography using an ion exchanger in which the beads form the backbone and contains active groups thereon. Anion exchangers or cation exchangers may be used. In a particularly preferred embodiment, a molecular sieve cation exchanger of the commercially available Sephadex brand sold as CM-Sephadex is suitable for this purpose. In this chromatographic step, the material is fractionated on the column in a solution of a buffer base of about 0.01 to 0.25 molar such as 0.2M ammonium acetate and preferably at a pH of about 4.0 to 6.0. An acid such as acetic acid may be added to obtain the desired pH. The extract passes through the column but the active material is retained by the beads. Thereafter, the column is developed with a linear concentration gradient to 0.5 to 1.0 molar, usually 0.55M ammonium acetate, which has also been brought to a pH of about 4.0 to 6.0. This means that while the fractionation was conducted at a pH of about 4.0 to 6.0, raising the molarity from about 0.2 to 0.55 in accordance with known linear concentration gradients results in removal of the active material which had been retained by the beads. The resulting product is then lyophilized and desalted on a Sephadex column in 0.1M ammonium bicarbonate as described and the resulting lyophilized void volume of these columns constitute the purified polypeptide. If the fraction is still impure on analysis of polyacrylamide disc electrophoresis, the ion exchange chromatography step can be repeated until purification is obtained. In this procedure, the term "lyophilized" means that the mixture is treated by freeze-drying to remove water and volatile buffers. The yield from the process will vary from batch to batch, but on the average, one kilogram of wet thymus will yield about 30 mg. of the polypeptide.

Isolation of the polypeptide of this invention from a plant source can proceed using generally the same steps. Thus, UBIP can be isolated from a plant such as celery by initially subjecting to the action of a juicer or beater to extract the juices from the solid materials followed by separation of the juices from the solids using a centrifuge or filter for example. The resulting supernatant is then subjected to molecular sizing by passage through a membrane under dialysis conditions to remove high molecular weight materials followed by passage of the resulting dialysate through a membrane to remove the lower molecular weight materials as described above. These steps can of course be run in reverse.

The resulting retentate is then lyophilized and fractionated by at least two passes through molecular exclusion chromatography as described above (e.g. with Sephadex G-50), to obtain materials having molecular weights in the range of about 4,000 to about 12,000. At this stage the lyophilized product may then be subjected to ion-exchange chromatography using either cation-exchangers or anion exchangers, as described above, to obtain the product. By lyophilizing and desalting the product is recovered. In this procedure, it has been found that the adsorption step using hydroxyl apatite is not necessary. The yields of product obtained from plants is usually lower than that achieved using animal cellular materials as source materials.

Figures 2, 3:
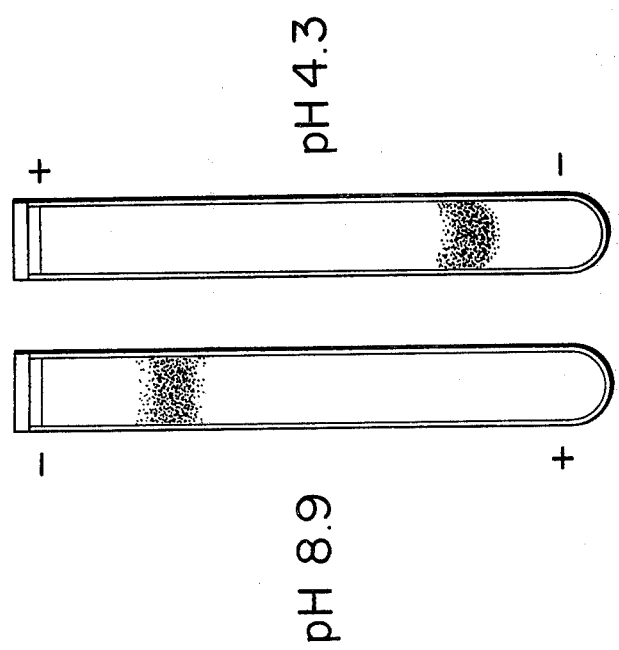
FIG. 2 shows a polyacrylamide gel from disc electrophoresis of the polypeptide at a pH of 8.9 and shows the major band present.
FIG. 3 shows a polyacrylamide gel from disc electrophoresis of the polypeptide at a pH of 4.3 and shows the major band present.

Reference is now made to FIGS. 2 and 3 accompanying this application which shows 7% polyacrylamide gels from disc electrophoresis of 0.2 mg. samples of the polypeptide which were used to monitor purity of the product. The results of this disc electrophoresis also serve to characterize the polypeptide of this invention. In each case the gels were fixed with trichloracetic acid and stained with Coomassie blue. As may be seen, one major band is present in each gel. At a pH of 8.9, the polypeptide had a relative mobility (Rf) with respect to bromphenol blue of 0.26. At a pH of 4.3, the polypeptide had a relative mobility (Rf) with respect to methyl green of 0.76.

As indicated, these purification procedures were monitored by analytical polyacrylamide disc electrophoresis which runs were as follows. Seven percent polyacrylamide gels were run at pH 8.9 and pH 4.3. Methyl green was used as a dye marker and the acid gels run towards the cathode and bromphenol blue was used in the basic gels run towards the anode. Spacer gels were not used, the samples being loaded in electrode buffer made up with the dye marker in 25% sucrose. The gels were fixed in 12.5% trichloractic acid, stained with Coomassie blue and the relative mobilities (Rf) were calculated with respect to the dye markers.

Electrophoresis of course is a known analytical procedure but it is pointed out generally that in the electrophoresis of molecular species, a sample containing a mixture of molecular species is deposited on an anticonvection medium which may be solid, semisolid or liquid, and a potential is applied across the sample and the medium. The different molecular species migrate at different rates through the medium so as to form generally flat zones, migrating in the direction of and being perpendicular to the electric field intensity, each zone containing a different species. After the different species have been separated, they are collected into different containers. If the medium is liquid, such as a liquid density gradient column, the different molecular species are generally collected with conventional fraction collectors that detect zones containing different species by light absorbance in the zone and channel the liquid containing each zone into a different container.

The medium is selected to provide the necessary separation in accordance with the ability of the medium to support different migration rates of different molecular species. Solids and semisolids are selected, under some circumstances, to serve as the medium rather than liquids because of special characteristics possessed by the solids and semisolids.

The molecular weight of the polypeptide was estimated to be 9,000 from molecular weight exclusion chromatography and amino acid composition.

Figure 4:
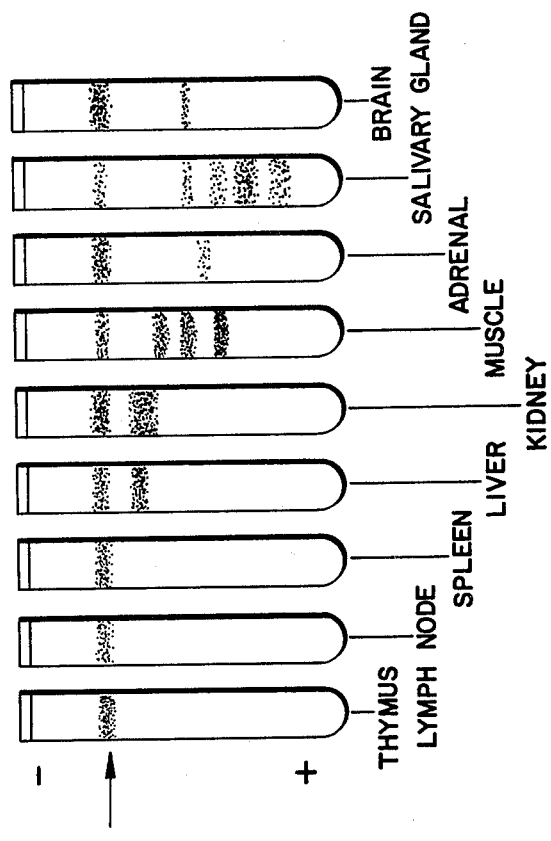
FIG. 4 shows polyacrylamide gels from disc electrophoresis at a pH of 8.9 using samples of product obtained from various guinea pig tissues.

Reference is now made to FIG. 4 accompanying this application which generally shows polyacrylamide gels from disc electrophoresis at a pH of 8.9 of 0.5 milligram samples of extracts of various guinea pig tissues. As will be seen in this Figure, the tissues subjected to disc electrophoresis in accordance with this invention were extracts from the thymus, lymph node, spleen, liver, kidney, muscle, adrenal, salivary, and brain. In obtaining the results shown in FIG. 4 each tissue was processed through the Sephadex-G50 step of FIG. 1 so that a fraction containing polypeptide having molecuar weights in the range of 4,000-12,000 had been obtained. In this Figure the arrow indicates the mobility of the polypeptide and a stained band is present in each gel at this position. In gels run at a pH of 4.3, a band with the mobility of the polypeptide was similarly found for each tissue so that each tissue tested contained a major polypeptide component with the same mobility at both pH's of 4.3 and 8.9. Thus, it is clear that the polypeptide was present in all materials tested.

As pointed out above, the polypeptide of this invention, is therapeutically useful in the treatment of humans and animals. Thus, since the new polypeptide has the capability for inducing the differentiation of lymphopoietic stem cells originating in the hemopoietic tissues to mature thymus-derived cells or T cells which are capable of involvement in the immune response to the body and also of stimulating the differentiation of B cells, the products of this invention are considered to have multiple therapeutic uses. Primarily, since the compound has the capability of carrying out certain of the indicated functions of the thymus it has application in various thymic function and immunity areas. A primary field of application is in the treatment of DiGeorge Syndrome, a condition in which there is a congenital absence of thymus. Injection of the polypeptide will overcome this deficiency. Another application is in agammaglobulinemia which is due to a defect of the putative B cell differentiative hormone of the body. Injection of the polypeptide will overcome this defect. Because of its biological characteristics, the polypeptide, being extremely active at low concentrations, is useful in assisting the collective immunity of the body in that it increases or assists in therapeutic stimulation of cellular immunity and humoral immunity and thereby become useful in the treatment of diseases involving chronic infection in vivo, such as fungal or mycoplasma infections, tuberculosis, leprosy, acute and chronic viral infections and the like. Further, UBIP is considered to be useful in any area in which cellular or humoral immunity is an issue and particularly where there are deficiencies in immunity such as in the DiGeorge Syndrome mentioned above. Further, because of the characteristics of the polypeptide, it has in vitro usefulness in inducing the development of surface antigens of T cells, in inducing the development of the functional capacity to achieve responsiveness to mitogens and antigens and cell collaborativity in enhancing the ability of B cells to produce antibodies. It has in vitro usefulness in inducing the development of B cells as measured by the development of surface receptors for complement. The peptide is also useful in inhibiting the uncontrolled proliferation of lymphocytes which are responsive to UBIP. An important characteristic of the polypeptide is its in vivo ability to restore cells with the characteristics of T cells and also its in vivo ability to restore cells with the characteristics of B cells. Therefore, the polypeptide is active in many areas as a result of its ability to enhance the immune response in the body.

It has also been found that the polypeptide is useful as a hypotensive agent as it provides beta-adrenergic stimulation and, on injection, lowers the blood pressure of the host to a significant degree.

The polypeptide of this invention is also useful for measuring various fluid levels of UBIP in the body such as the level of UBIP in serum and the like. In order to effect the measurement of such levels, a radioactive material, e.g. Iodine 125, Iodine 131, $C^{14}$ or $H^3$, is attached by chemical placement onto the UBIP molecule. One can also raise antibodies to the UBIP molecule by immunizing experimental animals. Thereafter, using the animal antibodies and the radioactive labeled UBIP molecule, one can then use standard radioimmunoassay techniques or radio-ligand displacement techniques to measure the amount of UBIP in serum, extracts or other fluids and the like. The reaction between UBIP and radioactive substance serves to replace at least one hydrogen on a tyrosine ring or an histidine molecule of UBIP to result in UBIP substituted on its tyrosine or histidine portion with the radioactive molecule, preferably $I^{125}$ or $I^{131}$.

The radioimmunoassay may be conducted by methods well known to the art as described for example in U.S. Pat. No. 3,646,346. In general, it should be understood that radioimmunological methods are based on the ability of an antibody to bind its protein antigen irrespective of whether the antigen is labeled with a radioactive isotope or not. The binding of labeled and unlabeled protein antigens takes place in proportion to the concentration of labeled and unlabeled proteins. The radioactivity of the labeled protein which is bound to the antibodies, and/or of the free, labeled protein in the sample liquid is measured. The amount of unlabeled competing protein can be determined from the obtained values by calculation or by direct comparison with a standard curve.

In principle, radioimmunological methods can be applied to proteins which are antigenic, capable of being purified and labeled with a radioactive isotope or a fluorescent group. The antibody bound protein has to be separated from the unbound protein.

A further important property of the polypeptide of this invention is that it is highly active in very low concentrations. Thus, it has been found that the polypeptide is active in concentrations ranging from as low as 1.0 nanogram per ml, and to be maximally active at concentrations from about 2.0 to 10 nanogram per ml. The carrier may be any of the well known carriers for this purpose including normal saline solutions, preferably with a protein diluent such as bovine serum albumin to prevent adsorptive losses to glassware at these low concentrations. The polypeptide is therapeutically active at a range of above about 0.1 mg/kg of body weight. For the treatment of DiGeorge Syndrome, the polypeptide is administered at the rate of about 0.1 to 10 mg/kg of body weight. Generally, the same dosage amounts may be used in the treatment of the other conditions or diseases mentioned.

The following examples are presented to illustrate the invention but it is not to be considered as limited thereto. In these examples and throughout the disclosure parts are by weight unless otherwise indicated.

EXAMPLE 1

The process steps of this example are summarized in FIG. 1. Bovine (calf) thymus was obtained fresh on wet ice, dissected clean and stored at −20° C. Batches were homogenized at 25% wet weight/volume in 0.1M ammonium bicarbonate using a Waring blender. The extract was heated to 70° C. for 30 minutes in a water bath and then centrifuged at 5,000 g. for 30 minutes. The supernatant was filtered through gauze and cotton and 0.1% thimerosal was added as a bacteriostatic agent since the subsequent steps were carried out at room temperature. The extract was processed through a Diaflo XM100A (pore size) membrane (Amicon) in a TC10 apparatus, a thin layer dialyzer (Amicon). The dialysate was then concentrated over a Diaflow UM2 membrane at 55 pounds per square inch, using a 402 stirred cell and a reservoir. Two liters were concentrated to 15 ml. This retentate was further fractionated on a 2.5 × 100 cm column of G-50 medium Sephadex (Pharmacia) in 0.1M ammonium bicarbonate. The fractions shown in FIG. 1 on the Sephadex G-50 column were lyophilized and rerun on the same column. The lyophilized fractions from this column were then fractionated by adsorption chromatography on hydroxyapatite (Biorad). A 500 mg load was dissolved in 0.005M sodium phosphate buffer, pH 6.8, and applied on a 2.5 × 30 cm column hydroxyapatite in the same buffer. The Thymin products of copending Application Ser. No. 429,202 eluted behind the void volume with 0.005M phosphate buffer; subsequently the concentration of the eluting buffer was raised to 0.05M. The fractions shown in FIG. 1 were then lyophilized and desalted on Sephadex G-25 in 0.1M ammonium bicarbonate. The lyophilized void volume of the G-25 column was taken up in 0.2M ammonium acetate which had been brought to pH 4.5 with acetic acid, and the sample was applied to a 0.6 × 30 cm column of CM-Sephadex in the same solvent. This was developed with a linear gradient to 0.55M ammonium acetate, pH 4.7. The fractions shown in FIG. 1 were lyophilized and desalted on G-25 Sephadex in 0.1M ammonium bicarbonate, and the lyophilized void volume constituted purified Ubiquitous Immunopoietic Polypeptide (UBIP).

Purity of the polypeptide preparations was assessed by polyacrylamide disc electrophoresis at pH 8.9 and pH 4.3 as described herein. With a load of 0.2 mg per gel there was a single band at both pH 8.9 (FIG. 2) and pH 4.3 (FIG. 3). The relative mobility (RF) with respect to bromphenol blue was 0.26 at pH 8.9 and the Rf with respect to methyl green was 0.76 at pH 4.3.

The molecular weight of the peptide was estimated to be 9,000 from molecular exclusion chromatography and amino acid composition. It was not possible to calculate recoveries or enrichments at each step of the isolation because purification was based solely on polyacrylamide disc electrophoresis criteria. On average 1 kg of wet thymus yielded 30 mg of product.

EXAMPLE 2

Bone marrow and spleen cells were obtained by flotation in BSA gradients similar to those used by Komuro and Boyse (Lancet, 1, 740-3, 1973). These cells were tested for their susceptibility to anti TL and Thy-1 ($\theta$) antibodies in a direct cytotoxicity test, using the uptake or trypan blue as a measure of cell death. In this cytotoxic test the induction of these antigens on mouse bone marrow cells in vitro was demonstrated. In this experiment, fractionated cells were incubated with 1.0 ng/ml of UBIP for 18 hours. At the end of this time 25 percent of these cells absorbed antibodies directed against either TL or Thy-1 ($\theta$) and were lysed by complement. The direct cytotoxic test does indicate the actual number of cells which have acquired sufficient antigen to be lysed by antiserum and complement. However, unless sufficient numbers of such cells are present they cannot be detected because of a substantial background usually found in such tests. Thus, TL induction could not be detected in unfractionated cells by the direct cytotoxic text, but when bone marrow or spleen cells were fractionated by flotation on discontinuous bovine serum albumen gradients, significant induction could be demonstrated in the least dense fractions of both tissues.

EXAMPLE 3

B Cell Induction

Mouse bone marrow or spleen to which was added EAC (erythrocytes plus rabbit anti-mouse erythrocyte antibodies plus mouse complement), was separated on BSA gradient (as above) and B and C layers were exposed in vitro to 1.0 ng of UBIP or medium without UBIP as a control. After 2 hours incubation, additional EACs were added and rosette-forming lymphocytes (complement receptor lymphocyte, CRL B cells) were enumerated. In presence of UBIP, approximately 25% of the B depleted precursor population differentiateed to CRL B cells and formed demonstrable rosettes with EAC.

The induction of B cells and T cells by UBIP is prevented by the addition of the B-adrenogeric blocking agent propanolol to the culture.

EXAMPLE 4

Hypotensive Action

An anesthetized 300 gram rat had its carotid artery and jugular vein cannulated with polyethylene cannulas containing heparinized saline. The arterial catheter was connected to a pressure transducer and the systemic blood pressure recorded. Injections were made into the venous catheter. Control injections of saline produced no effect. Injections of UBIP (0.5 mg) produced, after a delay of 2 minutes, a lowering of blood pressure of 15 mm mercury and this was sustained for 15 minutes.

The invention has been described herein with reference to certain prefered embodiments. However, as obvious variations thereon will become apparent to those skilled in the art, the invention is not to be considered as limited thereto.

What is claimed is:

1. A polypeptide which has the following amino acid sequence:

H$_2$N-MET-GLN-ILE-PHE-VAL-LYS-THR-LEU-THR-GLY-LYS-THR-ILE-THR-LEU-GLU-VAL-GLU-PRO-SER-ASP-THR-ILE-GLU-ASN-VAL-LYS-ALA-LYS-ILE-GLN-ASP-LYS-GLU-GLY-ILE-PRO-PRO-ASP-GLN-GLN-ARG-LEU-ILE-PHE-ALA-GLY-LYS-GLN-LEU-GLU-ASP-GLY-ARG-THR-LEU-SER-ASP-TYR-ASN-ILE-GLN-LYS-GLU-SER-THR-LEU-HIS-LEU-VAL-LEU-ARG-LEU-ARG-COOH.

2. A method for isolation of the polypeptide of claim 1 from bovine thymus which comprises homogenizing bovine thymus in buffered saline solution, heating at a temperature of about 60°–90° C., removing non-homogenized and insoluble materials, subjecting to filtration on membranes to remove materials having molecular weights above about 100,000 dalton, subjecting the resulting solution to dialysis to remove materials having molecular weights below about 2,000 to recover a solution containing materials having molecular weights of about 2,000 to 100,000, fractionating by molecular exclusion chromatography to recover a solution containing materials having molecular weights of about 4,000 to 12,000, fractionating by adsorption chromatography at a pH of about 6.8, then further fractionating by ion exchange chromatography and lyophilizing to recover the highly purified polypeptide as a powder.

3. A method according to claim 2 wherein the starting bovine thymus is homogenized in about 25% wet weight per volume of 0.1M ammonium bicarbonate.

4. A method according to claim 3 wherein heating is carried out at a temperature of about 70° C. for 30 minutes.

5. A method according to claim 4 wherein the homogenized mixture is centrifuged after heating at 5,000 g for 30 minutes to remove non-homogenized materials.

6. A method according to claim 5 wherein the supernatant recovered from the centrifugation step is filtered to remove insolubles and subjected to filtration over a membrane which separates materials having molecular weights above about 100,000 by permitting materials having molecular weights of less than about 100,000 to pass through the membrane.

7. A method according to claim 6 wherein further dialysis is conducted by contact with membrane which permits materials of molecular weights of less than about 2,000 to pass through the membrane while retaining the materials which have molecular weights above about 2,000.

8. A method according to claim 7 wherein the retentate from the second dialysis step is fractionated by molecular exclusion chromatography by passage of a solution through a column containing a cross-linked dextran molecular sieve which totally excludes materials having molecular weights above about 30,000 and totally includes materials having molecular weights of below about 1,500 and recovering materials having molecular weights of about 4,000–12,000 from the chromatography step.

9. A method according to claim 8 wherein the materials having molecular weights of about 4,000–12,000 are further fractionated by adsorption chromatography by passage through a column containing hydroxyl apatite in 0.005M phosphate buffer solution at a pH of about 6.8 wherein the materials are dissolved in the same phosphate buffer solution, and separation is obtained by differential sticking on the hydroxyl apatite, the active fractions obtained by raising the concentration of the buffer to 0.05M and the recovered fractions lyophilized and desalted.

10. A method according to claim 9 wherein the recovered materials are further fractionated by ion exchange chromatography in the presence of a cation exchanger at a concentration of about 0.01 to 1.0M and at a pH of about 4.0–6.0 or an anion exchanger at a concentration of about 0.01M and a pH of about 7.5 to 11.0, wherein the ion exchanger comprises a backbone with polymer groups thereon wherein the product sticks to the beads and is later removed by raising the molarity of the solution by linear concentration gradients.

11. A method according to claim 10 wherein the fractions recovered from the ion exchange chromatography are lyophilized and desalted to recover the final product.

12. A method for isolation of the polypeptide of claim 1 from celery comprising extracting the juices from the celery, contacting the juices with a membrane to exclude materials having molecular weights above about 100,000 and below about 2,000, subjecting the resulting materials to fractionation by molecular exclusion chromatography to obtain materials having molecular weights of about 4,000 to about 12,000, subjecting the resulting materials to ion-exchange chromatography followed by lyophilizing and desalting to obtain the polypeptide product.

* * * * *